(12) United States Patent
Winter

(10) Patent No.: US 7,396,973 B1
(45) Date of Patent: Jul. 8, 2008

(54) SIMULATED MOVING BED ADSORPTIVE SEPARATION PROCESS FOR HANDLING MULTIPLE FEEDSTOCKS

(76) Inventor: George R. Winter, 280 E. Harbor View Dr., Fond du Lac, WI (US) 54935

( * ) Notice: Subject to any disclaimer, the term of this patent is extended or adjusted under 35 U.S.C. 154(b) by 671 days.

(21) Appl. No.: 11/047,984

(22) Filed: Feb. 2, 2005

(51) Int. Cl.
*C07C 7/12* (2006.01)
(52) U.S. Cl. .................. 585/820; 585/822; 585/823; 585/824; 585/825; 585/829; 585/828
(58) Field of Classification Search ............... 585/820, 585/822, 825, 829
See application file for complete search history.

(56) References Cited

U.S. PATENT DOCUMENTS

| | | | |
|---|---|---|---|
| 2,985,589 | A | 5/1961 | Broughton et al. |
| 3,040,777 | A | 6/1962 | Carson et al. |
| 3,201,491 | A | 8/1965 | Stine et al. |
| 3,422,848 | A | 1/1969 | Liebman et al. |
| 3,686,342 | A | 8/1972 | Neuzil |
| 3,706,812 | A | 12/1972 | Derosset et al. |
| 3,715,409 | A | 2/1973 | Broughton |
| 3,732,325 | A | 5/1973 | Pharis et al. |
| 4,029,717 | A | 6/1977 | Healy et al. |
| 4,031,156 | A | 6/1977 | Geissler et al. |
| 4,313,015 | A | 1/1982 | Broughton |
| 4,402,832 | A | 9/1983 | Gerhold |
| 4,478,721 | A | 10/1984 | Gerhold |
| 4,642,397 | A | 2/1987 | Zinnen et al. |
| 4,793,984 | A | 12/1988 | Lok et al. |
| 5,912,395 | A | 6/1999 | Noe |
| 6,284,695 | B1 | 9/2001 | Winter |
| 6,303,021 | B2 | 10/2001 | Winter et al. |
| 6,342,649 | B1 | 1/2002 | Winter et al. |
| 6,380,438 | B1 | 4/2002 | Winter |
| 6,706,938 | B2 | 3/2004 | Roeseler et al. |
| 2001/0001451 | A1 | 5/2001 | Winter et al. |
| 2002/0071796 | A1 | 6/2002 | Winter et al. |

FOREIGN PATENT DOCUMENTS

WO     WO 95/07740     3/1995

OTHER PUBLICATIONS

Chemical Engineering Progress, vol. 66, No. 9, Sep. 1970, The Parex Process For Recovering Paraxylene, pp. 70-75.
Adsorptive Separations by Simulated Moving Bed Technology: The Sorbex Process, D.B. Broughton and S.A. Gembicki, pp. 115-124, 1980.

*Primary Examiner*—Tam M. Nguyen
(74) *Attorney, Agent, or Firm*—Ryan Kromholz & Manion S.C.

(57) ABSTRACT

The present invention discloses a means to improve the production capacity and feedstock handling flexibility of a simulated moving bed adsorptive separation process by introducing a second feed stream to the adsorbent chamber, such second feed stream comprising a feed material of a different concentration of the desired compound than the concentration of such desired compound in the first feed material stream. The introduction of this second feed material stream may be performed at any location on the adsorbent chamber between (i) a transfer point located immediately upstream of the point of the raffinate material stream withdrawal from the adsorbent chamber to (ii) a transfer point located immediately downstream of the point of extract material stream withdrawal from the adsorbent chamber. The specific transfer point used for the introduction of the second feed material stream will depend upon the concentration of the desired component in the second feed material stream.

23 Claims, No Drawings

SIMULATED MOVING BED ADSORPTIVE SEPARATION PROCESS FOR HANDLING MULTIPLE FEEDSTOCKS

BACKGROUND OF THE INVENTION

1. Field of the Invention

The subject invention relates to a process for the adsorptive separation of hydrocarbons. More specifically, the invention relates to a process for the continuous simulated countercurrent adsorptive separation of hydrocarbons.

The polyester fabrics and articles which are in wide use today are produced from a polymer of ethylene glycol and terephthalic acid. Terephthalic acid is produced by the oxidation of para-xylene. Para-xylene is typically recovered from a predominantly $C_8$ aromatic hydrocarbon fraction derived from various sources such as catalytic reforming by liquid-liquid extraction and/or fractional distillation. The para-xylene is commercially separated from a para-xylene containing feed stream, usually containing all four $C_8$ aromatic isomers, by either crystallization or adsorptive separation or a combination of these two techniques. Adsorptive separation is the newer technique and has captured the great majority of the market share of newly constructed plants for the production of para-xylene.

Essentially all of these adsorptive separation units use a simulated countercurrent movement of the adsorbent and the xylene containing feed stream. This simulation is performed using established commercial technology wherein the adsorbent is held in place in one or more cylindrical adsorbent chambers and the positions at which the streams involved in the process enter and leave the chambers are slowly shifted along the length of the beds. Normally there are at least four streams (feed, desorbent, extract, and raffinate) employed in this procedure. The location at which the feed and desorbent streams enter the chamber and the extract and raffinate streams leave the chamber are simultaneously shifted in the same direction at set intervals. Each shift in location of these transfer points delivers or removes liquid from a different bed within the chamber. This shifting could be performed using a dedicated transfer line for each stream at the entrance to each bed. However, this will greatly increase the cost of the process, and therefore the transfer lines are reused and each transfer line carries each one of the streams at some point in a cycle.

New and efficient chemical process technologies (e.g., XyMax®, Isomar®, PxMax®, and Tatoray® for the production of mixed aromatics, and Sarex XyMaxAE® for the production of mixed sugars) have presented the modern refiner with a dilemma of sorts, that is, how to accommodate the ever-changing availability of feedstocks of varying compositions in a process plant of relatively fixed architecture, without the need to perform major process piping and/or equipment revamp work.

2. Description of the Related Art

The general technique employed in the performance of a simulated moving bed adsorptive separation is well described in the open literature. For instance, a general description directed to the recovery of para-xylene was presented at page 70 of the September 1970 edition of Chemical Engineering Progress (Vol. 66, No. 9). A generalized description of the process with an emphasis on mathematical modeling was given at the International Conference on "Fundamentals Of Adsorption", Schloss Elmau, Upper Bavaria, Germany, on May 6-11, 1983, by D. B. Broughton and S. A. Gembicki. U.S. Pat. No. 4,029,717 issued to F. J. Healy et al. describes a simulated moving bed adsorptive separation process for the recovery of para-xylene from a mixture of xylene isomers. Numerous other available references describe many of the mechanical parts of a simulated moving bed system, including rotary valves for distributing various liquid flows, the internals of the adsorbent chambers, and control systems.

U.S. Pat. No. 3,686,342 issued to R. W. Neuzil describes the separation of para-xylene from mixed xylenes using simulated countercurrent adsorption employing a zeolitic adsorbent and para diethylbenzene as the desorbent. This combination is a good representation of a commercial operation for this particular separation.

For purposes of explaining the transfer line apparatus employed by the present invention, reference is made to U.S. Pat. No. 3,201,491 issued to L. O. Stine and D. B. Broughton and International Application WO 95/07740. That art includes a recognition that the presence of residual compounds in the transfer lines can have some detrimental effects on a simulated moving bed process, and which art addresses the flushing of the line used to deliver the feed stream to the adsorbent chamber as a means to increase the purity of the recovered extract or sorbate component. The foregoing patents teach the use of only one feed stream and a line flush only through the one transfer line most immediately previously used to convey feed to the adsorbent chambers to avoid contamination of the extract stream with raffinate components of the feed remaining in this line when it is subsequently used to withdraw the extract stream from the chamber. The foregoing references employ a desorbent rich stream to flush the contents of this transfer line back into the adsorbent chamber.

U.S. Pat. No. 3,732,325 issued to Broughton is directed to an improvement to a simulated moving bed adsorptive separation process characterized as related to the recycle of extract from the extract product stream to the purification zone. This patent teaches the use of only one feed stream. Broughton further teaches the introduction of that single feed material stream to the bottom of the purification zone.

U.S. Pat. No. 4,031,156 issued to P. R. Geissler et al. is directed to an improvement to a simulated moving bed adsorptive separation process characterized as related to flush streams used in the process. This reference is directed to flushing the interstitial void spaces between adsorbent particles in the adsorbent chamber. This patent teaches the use of dual desorbent streams and also teaches the use of only a single feed stream.

U.S. Pat. No. 5,912,395 issued to Noe, directed to an improvement to a simulated moving bed adsorptive separation process, is characterized as related to flush streams used in the process. This reference is directed to the flushing of the transfer line most recently used to withdraw a raffinate material stream from the adsorbent chamber only with a single feed material stream. This reference does not teach means to accommodate more than one feed stream material.

Relative selectivity, ($\beta$), as used throughout this specification is defined as the ratio of the two components in the adsorbed phase divided by the ratio of the same two components in the unabsorbed phase at equilibrium conditions. The equilibrium conditions are determined when the feed passing over a bed of adsorbent does not change composition, in other words, when there is no net transfer of material occurring between the unabsorbed and adsorbed phases. Relative selectivity can be expressed not only for one feed compound as compared to another but can also be expressed between any feed mixture component and the desorbent material.

Where relative selectivity of two components approaches 1.0, there is no preferential adsorption of one component by the adsorbent with respect to the other; they are both adsorbed to about the same degree with respect to each other. As $\beta$ becomes less than or greater than 1.0, there is a preferential adsorption by the adsorbent for one component with respect to the other. When comparing the selectivity of the adsorbent for component C over component D, a B larger than 1.0 indicates preferential adsorption of component C within the adsorbent. A β less than 1.0 indicates that component D is preferentially adsorbed leaving an unabsorbed phase richer in component C and an adsorbed phase richer in component D.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and, therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material, and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

SUMMARY OF THE INVENTION

The present invention discloses a means to improve the production capacity and feedstock handling flexibility of a simulated moving bed adsorptive separation process by introducing a second distinct feed stream to the adsorbent chamber, such second feed stream comprising a feed material of a different concentration of the desired compound than the concentration of such desired compound contained in the first feed material stream.

The present invention is an improvement to simulated moving bed adsorptive separation processes and includes the step of introducing into the process a second feed material stream of distinct composition from the first feed material stream, whereby the capacity and feedstock handling flexibility of the process is increased.

The introduction of the second feed material stream may be at any location on the adsorbent chamber between (i) a transfer point located immediately upstream of the point of the raffinate material stream withdrawal from the adsorbent chamber to (ii) a transfer point located immediately downstream of the point of extract material stream withdrawal from the adsorbent chamber. The specific transfer point used for the introduction of the second feed material stream will depend upon the concentration of the desired component in the second feed material stream.

According to one aspect of the present invention, the location of introduction of the second feed material stream to the process is selected from an available transfer point on the adsorbent chamber where the adsorbed component composition of the interstitial void space liquid is determined by analysis to most closely match that of the adsorbed component composition of the second feed material stream. For example, the second feed material stream may be introduced to the process via the transfer line just previously used to supply the first feed material stream to the adsorbent chamber. Alternately, depending on its concentration of the desired component, the second feed material may be introduced through the existing transfer line through which raffinate was just withdrawn from the chamber.

The present invention results in an increased capacity of the process unit and provides for more flexibility in the number and types of feed materials that may be processed therein, all without the need to perform major process piping and/or equipment revamp work.

A preferred application of the process is the separation of olefinic hydrocarbons and non-olefins from a feed mixture comprising olefins and non-olefins using a particular adsorbent and a particular desorbent. A further preferred application of the process is the separation of paraffinic hydrocarbons, such as branched chain paraffin hydrocarbons and straight chain paraffin hydrocarbons from a feed mixture comprising branched chain paraffin hydrocarbons and straight chain paraffin hydrocarbons using a particular adsorbent and a particular desorbent. A yet further preferred application of the process is the separation of sugars such as fructose and glucose from a feed mixture comprising fructose and glucose using a particular adsorbent and a particular desorbent. A most preferred application of the process is the separation of aromatic hydrocarbons such as the separation of para-xylene from a feed mixture comprising at least two xylene isomers, including the para-isomer, using a zeolitic adsorbent and a particular desorbent.

It is an objective of the subject invention to provide an improved process for the simulated moving bed adsorptive separation of chemical compounds. It is a further objective to provide an improved process for the adsorptive separation of aromatic hydrocarbons. It is another objective of the subject invention to provide a process which increases the capacity of a simulated moving bed adsorptive separation process to recover a selectively adsorbed compound. It is a specific objective to increase the capacity of a simulated moving bed process unit to recover para-xylene from a feed stream comprising a mixture of xylene isomers. It is yet another specific objective of the present invention to provide for more flexibility in the number and types of feed materials that may be processed in a simulated moving bed unit to recover paraxylene from a feed stream comprising a mixture of xylene isomers, with less need to perform major process piping and/or equipment revamp work, thereby resulting in savings of time, manpower, material, and money.

These and other objectives are achieved by supplying a second feed material stream into the adsorbent chamber of a simulated moving bed process unit in accordance with the present invention.

Other advantages, benefits, and features of the invention will become apparent to those skilled in the art upon reading the detailed description of the invention.

DETAILED DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structures. The scope of the invention is defined in the claims appended hereto.

In numerous processes described in the patent literature, zeolitic adsorbents are used to separate various hydrocarbons and other chemical compounds such as chlorinated or un-chlorinated aromatics. Another example of hydrocarbon separation by class is the recovery of either paraffins or aromatics from a feed mixture comprising both aromatics and paraffins. The subject invention can be employed in these separations or in the separation of other compounds including choral compounds for use in pharmaceuticals and fine chemicals, oxygenates such as alcohols and ethers, carbohydrates such as sugars, and dimethyl naphthalenes. Efficiency is a more important factor in the commercial success of small units producing separated choral compounds and other fine chemicals than for large scale units such as those producing para-xylene. The following description of the subject invention will, however, be presented basically in terms of the separation of various isomers of dialkyl substituted monocyclic aromatics, such as para-xylene isomer, from the other xylene isomers, which is normally performed in large scale units.

During the adsorption step of the process a feed mixture containing a mixture of isomers, such as xylene isomers, is contacted with the adsorbent at adsorption conditions and the desired isomer is selectively adsorbed and retained by the adsorbent while the other components of the feed mixture are relatively unabsorbed. The feed mixture may contain compounds other than isomers of the desired compound. For instance, a mixed xylene feed stream may contain ethylbenzene and/or $C_9$ aromatics. When the adsorbent contains a near equilibrium loading of the more selectively adsorbed isomer, it is referred to as a "rich" adsorbent. The unabsorbed raffinate components of the feed mixture are then removed from the interstitial void spaces between the particles of adsorbent and from the surface of the adsorbent. The adsorbed isomer is then recovered from the rich adsorbent by contacting the rich adsorbent with a stream comprising a desorbent material at desorption conditions. The desorbent displaces the desired isomer to form an extract stream, which is transferred to a fractionation zone for recovery of the desired isomer from the mixture containing the desired isomer and desorbent.

Processes for the adsorptive separation of para-xylene from other xylene isomers by simulated countercurrent adsorption are both widely described and widely practiced. These processes typically include at least three or four separate steps which are performed sequentially in separate zones within a mass of adsorbent retained in one or more vertical cylindrical adsorption chambers. The singular noun "chamber" is used herein to refer to one or more chambers. Each of these zones normally is formed from a plurality of beds of adsorbent, sometimes commonly referred to as either "beds" or "sub-bed", with the number of beds per zone ranging from 2 or 3 up to 8-10. The most widely practiced commercial process units typically contain about 24 beds. All of the beds are contained in one or more vertical vessels referred to herein collectively as the adsorbent chamber. The beds are structurally separated from one another by a horizontal liquid collection/distribution grid. Each grid is connected to a transfer line defining a transfer point at which process streams enter and leave the vertical adsorption chamber.

Briefly, in the first step, normally labeled as occurring in the adsorption zone or Zone I of the chamber, the feed stream is contacted with a selective adsorbent which adsorbs the desired isomer. This step removes the desired isomer from the flowing liquid. The depleted liquid and any desorbent which becomes admixed with it during passage through the adsorption zone are removed from the process as a process stream referred to as the raffinate stream.

The adsorbent in Zone I is surrounded by liquid which contains the undesired isomer(s), that is, with raffinate. This liquid is removed from the adsorbent in Zone II, referred to as a purification zone. In the purification zone the undesired raffinate components are flushed from the void volume and desorbed from the pore volume of the adsorbent bed by a material which is easily separated from the desired component by fractional distillation.

In Zone III of the adsorbent chamber the desired isomer is released from the adsorbent by exposing and flushing the adsorbent with a liquid called desorbent. The released desired isomer and accompanying desorbent are removed from the adsorbent in the form of a stream referred to herein as the extract stream.

Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of the liquid in Zone III by the liquid in Zone I by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563.

It is readily apparent that when a transfer line which is being used to transport a particular stream is left idle at the end of a step it will remain full of the compounds forming that stream until these compounds are removed from the line by a subsequent flowing stream. The residual compounds left in the now unused transfer line will therefore be either withdrawn from the process as the initial part of a process stream flowing from the process, or forced into the adsorbent chamber when the transfer line carries a stream into the adsorbent chamber. As described above, those working in this art have recognized that the presence of these residual compounds in the transfer lines can have some detrimental effects on the performance of a simulated moving bed adsorptive separation process.

The precise amount of material which is used to flush a given transfer line beyond the amount required to flush the transfer line of its prior contents is not critically important, but measurement of this quantity is required. That is to say, it is believed there is only minimal back-mixing of liquids in the transfer lines, and that therefore the amount of flush liquid need not greatly exceed the total volume of the transfer line which is to be flushed. The transfer "line" may be in several parts linked together by valves or other connecting devices. A broad range of the required quantity of the flush liquid is from about 0.4 to about 2.5 times this total volume. A preferred quantity of the feed stream used to flush the raffinate line and any associated valving is from 0.5 to about 1.5 times this total volume.

In addition, as described above, since adsorption is an equilibrium mass-transfer process, the composition of the liquid in the selective pore volume of the adsorbent can be affected by changing the concentration of the liquid in the non-selective interstitial void volumes and pores of the adsorbent. Thus, most designers include a recycle stream to the upstream end of the purification zone to reflux para-xylene, which refluxing is expected to increase the concentration of para-xylene in the selective pore volume.

Typical commercial practice involves the use of, in addition to the feed, raffinate, desorbent, and extract transfer lines, one or more additional transfer lines to accommodate the implementation of the above described para-xylene RECYCLE, LINE FLUSH and FLUSH OUT streams.

In accordance with the present invention, a stream of a second feed material is introduced into the chamber in either Zone II or Zone I as those zones are described above. The stream of the second feed material has a concentration of the desired compound that is different than the concentration of the desired compound in the first feed material stream. For maximum benefit, the second feed material is introduced at the location in the chamber at which the concentration of the desired compound in the second feed material matches the concentration along the concentration profile of the adsorbed component composition of material in the interstitial void inside the chamber. Accordingly, depending on the relative concentrations of the first and second feed materials, the second feed material stream may be introduced at a location either upstream or downstream of the location of the introduction of the first feed material stream. The present invention is thus designed to minimize changes to the concentration profiles in the adsorbent chamber at the transfer point on the adsorbent chamber where the second feed material stream is introduced, thus minimizing the quantity of the desired product that is contained in the raffinate stream.

It must be recognized that the subject invention is not directed to the technique of merely flushing a transfer line which carries liquid to and from the adsorbent chamber. It is therefore not limited merely to technology which involves flushing the beds of adsorbent material.

It must be further recognized that the subject invention is not directed to the technique of recycling either an extract product material stream or a raffinate product material stream back to the adsorbent chamber. It is therefore not limited to technology which merely involves recycling of such materials to the beds of adsorbent material.

It must be still further recognized that the subject invention is not directed to the technique of processing single feed material streams through the adsorbent chamber, but rather the processing of two or more feed material streams of differing compositions. It is therefore not limited to technology which involves the processing of single feed material streams to the beds of adsorbent material.

The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber. This is primarily important in describing the transfer line for the second feed stock that is used in the present invention. As will be described in detail below, in the present invention it is most preferably the transfer line which was just used to inject the first feed material stream before the most recent incrementing of the transfer points during the simulation of countercurrent moving bed operation. Therefore, it is the transfer line just upstream of the transfer line presently used as the first feed material stream transfer line. This may be one or several physical bed transfer lines away from the bed transfer line being used for feed.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent, while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

In many cases, the concentration of the desired component in the second feed material stream is anticipated to be higher than the concentration in the first feed material stream. In those cases, the second feed material stream is introduced into the chamber upstream of the first feed material stream. Further, to optimize the overall performance of the chamber and its related equipment, it is highly desirable to utilize existing transfer lines to the extent possible.

Therefore, in the preferred embodiment, the second feed material stream is introduced into the chamber through the existing transfer line that was just flushed after carrying the first feed material stream to the chamber. That design minimizes the work and expense required to practice the invention without significant adverse effect on its benefits.

To be clear in the distinction between the present invention and the prior art, the use of an existing transfer line to carry either a pure or recycled desorbent material, extract material, single feed material, or raffinate material, as the case may be, in the practice of the present invention is merely a means to the end of the present invention. In fact, furthermore, the use of the single feed material or recycled extract material or raffinate material in the prior art is always present in the prior art only in conjunction with a single feed material, contrary to the practice of the present invention.

In further distinction of the present invention over the prior art, with respect to the introduction of the second feed material stream, larger amounts of material used as a flushing medium are generally beneficial as larger quantities of second feed material through the transfer line increase the feed processing capacity in the process unit, as it must be recognized that the flush material is passed into the adsorbent chamber at a transfer point on the adsorbent chamber where the adsorbed component composition of the interstitial void space liquid is determined by analysis to most closely match the adsorbed component composition of the second feed material stream.

Countercurrent simulated moving bed systems are described in many available references, such as U.S. Pat. No. 2,985,589, incorporated herein by reference for its teaching of the practice of simulated moving bed adsorptive separation processes. Cyclic advancement of the input and output streams of this simulation can be accomplished by a manifolding system or by rotary disc valves as shown in U.S. Pat. Nos. 3,040,777 and 3,422,848. Equipment utilizing these principles can vary in size from the pilot plant scale shown in U.S. Pat. No. 3,706,812 to commercial petrochemical plant scale, with flow rates ranging from a few cc per hour to many thousands of gallons per hour. Large scale plants normally employ rotary valves having a port for each transfer line while small scale and high pressure units tend to use valves having only two or three ports. The present invention will normally be employed in an adsorptive separation process which simulates countercurrent movement of the adsorbent and surrounding liquid, but it may also be practiced in a cocurrent continuous process like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated by reference herein, for additional description of these adsorption fundamentals.

The practice of the subject invention requires no significant changes in adsorbent or desorbent composition. Further, in a preferred embodiment, no significant mechanical changes are required in the adsorbent chambers. For up to two distinct feeds, no new input streams are needed and the output streams are also essentially unchanged except for the added improvement of a reduction in the desorbent content of the output streams, thereby reducing the load on downstream product recovery units. The only significant required change to the process equipment is that needed to deliver a controlled quantity of the second feed material stream to the second feed material stream transfer line. These changes are preferably made in and near the equipment used to control the flow of the process streams to and from the adsorbent chamber in the case of the use of the flush transfer line essentially in the same manner as in the previously referred to Stine et al. patent, and in the case of the recycle transfer line, essentially in the same manner as in the previously referred to Broughton U.S. Pat. No. 3,732,325. That is, the subject process may be implemented on an existing process unit by a modification in the equipment which directs fluid flow. The amount of the respective material is preferably controlled by a single valve each on a single respective line through which the material in question flows before entering the line and valve system to be in question.

The practice of the subject invention is not believed related to or limited to the use of any particular adsorbent or adsorbent/desorbent combination. The only limitation is the effectiveness of the adsorbent/desorbent combination in the desired separation. Examples of adsorbents which may be used in the process of this invention include non-zeolitic molecular sieves including carbon-based molecular sieves, silicalite, and the crystalline aluminosilicates molecular sieves classified as X and Y zeolites. The adsorbent may or may not be a zeolite. The sorptive properties of one non-zeolitic molecular sieve, ALPO-5, are described in a paper printed in the Journal of Catalysis 111, 23-40 (1988). Details on the composition and synthesis of many of these microporous molecular sieves are provided in U.S. Pat. No. 4,793,984, which is incorporated by reference herein for this teaching. Information on adsorbents may also be obtained from U.S. Pat. Nos. 4,385,994; 4,605,492; 4,310,440; and, 4,440,871. Differing sieve/desorbent combinations are used for different separations. For instance, X zeolites, specifically X zeolites exchanged with barium or barium and potassium ions at their exchangeable sites, are the preferred adsorbents for p-xylene recovery from xylene mixtures.

The composition and structure of Zeolites is well know in the art and described in the references cited herein, hereby being incorporated herein by reference.

Those skilled in the art will appreciate that the performance of an adsorbent is greatly influenced by a number of factors not related to its composition such as operating conditions, feed stream composition, water content of the adsorbent, and the desorbent composition. The optimum adsorbent composition is therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500 degrees C. under an inert gas purge such as nitrogen for a period of time sufficient to achieve a constant weight. For p-xylene recovery it is often preferred that the water content of the adsorbent results in an LOI at 500 degrees C. of less than 7.0% and preferably within the range of from 0 to 6.5 wt %.

The zeolite will ordinarily be in the form of small crystals present in the particles in amounts ranging from about 75 to about 98 wt. % of the particle based on volatile-free composition. Volatile-free compositions are generally determined after the adsorbent has been calcined at 900 degrees C. in order to drive off all volatile matter. The remainder of the adsorbent will generally be the inorganic matrix present in intimate mixture with the small particles of the zeolite material. This matrix material may be an adjunct of the manufacturing process for the zeolite (for example, from the intentionally incomplete purification of the zeolite during its manufacture), or it may be added to relatively pure zeolite, but in either case its usual purpose is as a binder to aid in forming or agglomerating the zeolite into the hard particles.

Benzene, toluene, and p-diethylbenzene are normally described as suitable desorbents for para-xylene recovery in the references, with p-diethylbenzene (p-DEB) having become a commercial standard for the separation. P-DEB is a "heavy" desorbent (higher boiling than p-xylene) which allows for easier recovery of the desorbent from the extract and raffinate streams by fractional distillation.

At least portions of the extract stream and the raffinate stream are passed to separation means, typically fractional distillation columns, where at least a portion of desorbent material is recovered to produce an extract product and a raffinate product. The terms "extract product" and "raffinate product" mean products produced by the process containing, respectively, an extract component and a raffinate component in higher concentrations than those found in the extract stream and the raffinate stream. The term "rich" is intended to indicate a concentration of the indicated compound or class of compounds greater than the concentration in the feed 50 mole percent.

Feed mixtures which can be utilized in the process of this invention are typically prepared by fractional distillation. They may comprise para-xylene and at least one other $C_8$ aromatic isomer, and may also contain other hydrocarbons. Thus, the feed mixtures to the process of this invention can contain sizable quantities of $C_6$, $C_7$, and $C_9$ aromatics and may also contain quantities of straight or branched chain paraffins, cycloparaffins, or olefinic material having boiling points relatively close to the desired xylene isomer. The desired xylene may be the para, meta, or ortho isomer. The feed material streams can alternatively contain a mixture of isomers of other aromatic or paraffinic hydrocarbons. Some specific examples are cresol isomers, cymene isomers, and dimethyl naphthalene isomers. The subject process may also be employed to separate classes of compounds such as olefins from paraffins or straight chain paraffins from nonstraight chain; e.g., iso and cycloparaffins. The subject process may also be employed to separate classes of sugar compounds such as fructose from glucose.

Mixtures containing substantial quantities of para-xylene, other $C_8$ aromatic isomers, and other hydrocarbons and $C_9$ aromatics generally are produced by catalytic naphtha reforming and/aromatic hydrocarbon isomerization processes. These processes are well known in the refining and petrochemical arts. In a catalytic naphtha reforming process a naphtha boiling range feed is contacted with a platinum and halogen-containing catalyst at severities selected to produce an effluent containing $C_8$ aromatic isomers. Generally, the reformate is then fractionated to concentrate the $C_8$ aromatic isomers into a $C_8$ fraction which will also contain co-boiling non-aromatics and some $C_7$ and $C_9$ aromatics. Feed mixtures for the process of this invention may also be obtained from isomerization and transalkylation processes. For instance, the transalkylation of mixtures of $C_7$ and/or $C_9$ aromatics produces xylene isomers. Xylene mixtures recovered from the adsorption zone which are deficient in one or more isomers can be isomerized, at isomerization conditions, to produce an effluent containing $C_8$ aromatic isomers, which can then be recycled to the adsorption zone for separation.

Adsorption conditions in general include a temperature range of from about 20 degrees to about 250 degrees C., with from about 60 degrees to about 200 degrees C. being more preferred for para-xylene separation. Adsorption conditions also include a pressure sufficient to maintain liquid phase, which may be from about atmospheric to 600 psig. Desorption conditions generally include the same range of temperatures and pressure as used for adsorption conditions. Different conditions may be preferred for other extract compounds.

EXAMPLE

In order to verify the improvement expected from the present invention, a comparison was performed using a computerized model which has been shown to accurately predict and correlate with the actual operation of a given commercial scale simulated moving bed adsorptive separation unit used to recover para-xylene from a mixture of xylene isomers.

In this experiment, as is often the case commercially, it is assumed that the operator of the commercial process unit would have available to it two distinct sources of para-xylene containing feed stock. The simulated unit was assumed to have twenty-four beds of adsorbent which may commercially be divided between two columns and utilize a twenty-four port rotary valve to direct the flow of the process streams. For the purpose of explaining with further clarity the implementation and benefits of the present invention, but not meant to imply any limitation or requirement thereof, feed A is a first feed material stream originating from the isomerate xylene splitter column distillate product of a xylene isomerization process unit, and Feed B is a second feed material stream originating from the xylene column distillate product of a Toluene Disproportionation process unit. The two feed material streams contain the respective components as set out in Table 1.

Case I demonstrates the utility and benefits of the present invention by utilizing separate transfer points for the introduction of the two distinct feed material streams to the process unit of the present invention, while Case II shows the prior art method of mixing the two feed material streams into one combined feed material stream before the introduction thereof into the prior art process unit via a single transfer point feed material stream. In addition, the refiner would have as its objective to process in the process unit to recover 99.75 wt % purity para-xylene product at an acceptable recovery.

In addition, as shown in Case I, Table 1 shows the compositions of the first feed material stream and the second feed material stream of the present invention as well as the single combined feed material stream of the prior art. The model produced the different required adsorbent to feed ratios needed for the process unit to produce an extract having the required para-xylene recovery. These adsorbent to feed ratios were 0.95 using the combined feed material stream method of the prior art and were 0.75 using the first feed material stream and the second feed material stream of the present invention with the second feed material stream entering the adsorbent chamber through the line flush transfer line. These ratios translate into an approximately 27 volume percent increase in throughput capacity of the process unit.

TABLE 1

| | Feed Composition (wt. %) | | | | |
|---|---|---|---|---|---|
| | | | Case | | |
| | | | I (Prior Art) Feed (Mixed) | II (Present Invention) | |
| | I and II | | | | |
| Component | Extract | Raffinate | A + B | Feed A | Feed B |
| Non-aromatics | 0.00 | 0.4 | 0.2 | 0.3 | 0.0 |
| Ethylbenzene | 0.13 | 19.3 | 12.6 | 15.5 | 1.0 |
| Para-xylene | 99.75 | 1.2 | 35.8 | 22.5 | 89.0 |
| Meta-xylene | 0.08 | 54.5 | 35.4 | 42.2 | 8.0 |
| Ortho-xylene | 0.04 | 24.6 | 16.0 | 19.5 | 2.0 |

What is claimed is:

1. A simulated countercurrent adsorptive separation process for separating a desired chemical compound from a mixture of two or more chemical compounds comprising the steps of:
   a. providing a first feed material having a first concentration of the desired chemical compound;
   b. providing a second feed material having a second concentration of the desired chemical compound;
   c. providing a multi-bed adsorbent chamber;
   d. introducing a stream of the first feed material into the adsorbent chamber at a first transfer point;
   e. flowing the first feed material through the adsorbent chamber in a downstream direction;
   f. adsorbing the desired chemical compound from the first feed material by a selected adsorbent and thereby producing a first raffinate material;
   g. removing the first raffinate material from the adsorbent chamber at a second transfer point located in a downstream direction from the first transfer point;
   h. introducing a stream of the second feed material into the adsorbent chamber at a third transfer point in the upstream direction of the second transfer point;
   i. flowing the second feed material through the adsorbent chamber in the downstream direction;

j. adsorbing the desired chemical compound from the second feed material by the selected adsorbent and thereby producing a second raffinate material;
k. removing the second raffinate material from the adsorbent chamber at the second transfer point; and
l. removing a first desired chemical compound from the adsorbent chamber at a fourth transfer point located in a downstream direction from the second transfer point.

2. The process of claim 1 wherein the steps of providing first and second feed materials comprise the step of providing a first feed material having a higher concentration of the desired chemical compound than the second feed material.

3. The process of claim 1 wherein the steps of providing first and second feed materials comprise the step of providing a first feed material having a lower concentration of the desired chemical compound than the second feed material.

4. The process of claim 1 wherein the step of introducing a stream of the second feed material comprises the step of locating the third transfer point in the upstream direction from the first transfer point.

5. The process of claim 1 wherein the step of introducing a stream of the second feed material comprises the step of locating the third transfer point in the downstream direction from the first transfer point.

6. The process of claim 1 wherein:
a. the step of flowing the first feed material through the adsorbent chamber in a downstream direction comprises the step of changing the concentration of the desired chemical compound in the first feed material in response to the first feed material flowing in the downstream direction; and
b. the step of introducing a stream of the second feed material comprises the step of locating the third transfer point at a location on the absorbent chamber whereat the concentration of the desired chemical compound of the first feed material flowing through the adsorbent chamber substantially matches the concentration of the desired chemical compound of the second feed material.

7. The process of claim 1 wherein:
a. the step of providing an adsorbent chamber comprises the step of providing a fifth transfer point in the adsorbent chamber in the upstream direction from the first transfer point;
b. the simulated countercurrent adsorptive separation process comprises the further step of introducing a flush material into the adsorbent chamber at the fifth transfer point; and
c. the step of introducing the stream of the second feed material comprises the step of introducing the stream of the second feed material through the fifth transfer point subsequent to introducing the flush material into the adsorbent chamber at the fifth transfer point.

8. The process of claim 1 wherein:
a. the step of flowing the stream of the first feed material in the downstream direction comprises the step of changing the concentration of the desired chemical compound in the first feed material and thereby producing a concentration profile of the first feed material between the first and second transfer points; and
b. the step of inserting a stream of the second feed material comprises the steps of:
i. measuring the concentration of the desired chemical compound in the first feed material along the concentration profile thereof;
ii. determining the location in the adsorbent chamber at which the concentration of the desired chemical compound in the first feed material matches the concentration of the desired chemical compound of the second feed material; and
iii. introducing the stream of the second feed material at the location in the adsorbent chamber at which the concentration of the desired chemical compound in the first feed material matches the concentration of the desired chemical compound of the second feed material.

9. The process of claim 1 wherein the step of providing first and second feed materials comprises the step of providing first and second feed materials each comprised of $C_8$ aromatic hydrocarbons.

10. The process of claim 1 wherein the step of providing first and second feed materials comprises the step of providing first and second feed materials each comprised of xylenes.

11. The process of claim 1 wherein the step of providing first and second feed materials comprises the step of providing first and second feed materials each comprised of a mixture of paraffins and aromatics.

12. The process of claim 1 wherein the step of providing first and second feed materials comprises the step of providing first and second feed materials each comprised of a mixture of normal and non-normal paraffins.

13. The process of claim 1 wherein the step of providing first and second feed materials comprises the step of providing first and second feed materials each comprised of a mixture of chiral isomers which are to be separated.

14. The process of claim 1 wherein the step of providing first and second feed materials comprises the step of providing first and second feed materials each comprised of cymene isomers.

15. The process of claim 1 wherein the step of providing first and second feed materials comprises the step of providing first and second feed materials each comprised of a mixture of sugars.

16. The process of claim 1 wherein the step of providing first and second feed materials comprises the step of providing first and second feed materials each comprised of a mixture of fructose and glucose.

17. The process of claim 1 wherein the step of providing first and second feed materials comprises the step of providing first and second feed materials each comprised of a mixture of dimethyl naphthalene isomers.

18. In a simulated countercurrent adsorptive separation process for separating a desired chemical compound from a first feed material comprising two of more chemical compounds wherein a stream of the first feed material, a flushing stream, a recycle stream, and a desorbent stream are introduced into a multiple-bed adsorbent chamber at first, second, third, and fourth transfer points, respectively; and wherein a line flush, raffinate stream, and extract stream are individually removed from the adsorbent chamber at fifth, sixth, and seventh transfer points, respectively,
the improvement wherein:
a. a second feed material is provided having two of more chemical compounds and containing the desired chemical compound; and
b. a stream of the second feed material is introduced into the adsorbent chamber at a selected transfer point that is located between the sixth and seventh transfer points.

19. The simulated countercurrent adsorptive separation process of claim 18 wherein:
a. the second feed material is provided with a concentration of the desired chemical compound that is less than the concentration of the desired chemical compound in the first feed material; and b. the selected transfer point is located between the first and seventh transfer points.

20. The simulated countercurrent adsorptive separation process of claim 18 wherein:
   a. the second feed material is provided with a concentration of the desired chemical compound that is greater than the concentration of the desired chemical compound in the first feed material; and
   b. the stream of the second feed material is introduced into the adsorbent chamber at a transfer point located between the first and sixth transfer points.

21. The simulated countercurrent adsorptive separation process of claim 20 wherein:
   a. the concentration of the desired chemical compound in the first feed material is measured between the first and sixth transfer points; and
   b. the selected transfer point is located whereat the concentration of the desired chemical compound in the first feed material matches the concentration of the desired chemical compound in the second feed material.

22. The simulated countercurrent adsorptive separation process of claim 18 wherein the selected transfer point is located at the transfer point that was most recently the first transfer point.

23. The simulated countercurrent adsorptive separation process of claim 18 wherein the selected transfer point is located at the transfer point that was most recently the second transfer point.

* * * * *

UNITED STATES PATENT AND TRADEMARK OFFICE
CERTIFICATE OF CORRECTION

PATENT NO. : 7,396,973 B1 Page 1 of 1
APPLICATION NO. : 11/047984
DATED : July 8, 2008
INVENTOR(S) : George R. Winter It is certified that error appears in the above-identified patent and that said Letters Patent is hereby corrected as shown below:

Column 14, line 47, after "two" delete "of" and insert -- or --

Column 14, line 56, after "two" delete "of" and insert -- or --

Signed and Sealed this

Eleventh Day of November, 2008

JON W. DUDAS
*Director of the United States Patent and Trademark Office*